(12) United States Patent
Calleri

(10) Patent No.: US 12,736,517 B2
(45) Date of Patent: Sep. 15, 2026

(54) GEOLOGICAL SAMPLE INTERPRETATION THROUGH SYSTEMATIC ANALYSIS OF COLOUR, ELEMENTAL DATA AND ELECTROMAGNETIC OBSERVATION

(71) Applicant: GEOLOG S.R.L., San Giuliano Milanese (IT)

(72) Inventor: Antonio Calleri, San Giuliano Milanese (IT)

(73) Assignee: Geolog S.R.L., San Giuliano Milanese (IT)

( * ) Notice: Subject to any disclaimer, the term of this patent is extended or adjusted under 35 U.S.C. 154(b) by 488 days.

(21) Appl. No.: 18/358,816

(22) Filed: Jul. 25, 2023

(65) Prior Publication Data

US 2024/0036023 A1 Feb. 1, 2024

(30) Foreign Application Priority Data

Jul. 26, 2022 (IT) ........................ 102022000015648

(51) Int. Cl.
*G06F 18/241* (2023.01)
*G01N 33/24* (2006.01)

(52) U.S. Cl.
CPC ........... *G01N 33/24* (2013.01); *G06F 18/241* (2023.01)

(58) Field of Classification Search
CPC ...... E21B 2200/22; E21B 41/00; E21B 43/30; E21B 7/04; E21B 2200/20; E21B 43/00; E21B 47/0025; E21B 47/04; E21B 47/138; E21B 49/00; E21B 49/003; E21B 49/005; E21B 1/00; E21B 3/00; E21B 4/00; E21B 6/00; E21B 7/00; E21B 10/00; E21B 11/00; E21B 12/00; E21B 15/00; E21B 17/00; E21B 19/00; E21B 21/00; E21B 23/00; E21B 25/00; E21B 27/00; E21B 28/00; E21B 29/00; E21B 33/00; E21B 31/00; E21B 34/00; E21B 35/00; E21B 44/00; G01V 1/345; G01V 20/00; G01V 2210/66;

(Continued)

(56) References Cited

U.S. PATENT DOCUMENTS 6,324,474 B1 * 11/2001 Beisner ................. G01S 19/072
342/357.31
11,740,382 B2 * 8/2023 Mohler .................. G01V 5/281
378/1

(Continued)

OTHER PUBLICATIONS

Italian Search Report dated Mar. 21, 2023, issued in Italian Application No. 102022000015648, filed Jul. 26, 2022.

(Continued)

*Primary Examiner* — Daniel Previl
(74) *Attorney, Agent, or Firm* — Workman Nydegger

(57) ABSTRACT

A method for the classification of geological materials into similar facies includes: determining the elemental metric for each geological sample from a geographical location; determining a colour metric for each geological sample from a geographical location; setting an initial classification framework based on the availability and quality of the colour metric; using the initial classification framework as the target for a machine learning process; applying the trained machine learning process on geological samples from another geographical location for the classification of said geological samples from another geographical location.

15 Claims, 5 Drawing Sheets

(58) Field of Classification Search

CPC ........ G01V 1/282; G01V 1/301; G01V 1/302; G01V 1/34; G01V 1/50; G01V 11/00; G01V 3/20; G01V 3/38; G01V 1/00; G01V 3/00; G01V 5/00; G01V 7/00; G01V 8/00; G01V 9/00; G01V 2210/00; G01V 2200/00; G01V 99/00; G01V 15/00; G06N 20/00; G06N 3/00; G06N 5/00; G06N 7/00; G06N 10/00; G06N 99/00; G06N 3/02; G06Q 10/04; G06Q 10/06375; G06Q 10/067; G06Q 50/02; G06Q 10/00; G06Q 20/00; G06Q 30/00; G06Q 40/00; G06Q 50/00; G06Q 90/00; G06Q 99/00; G06Q 2220/00; G06Q 2230/00; G06Q 2240/00; G06Q 2250/00; E21D 11/18; E21D 9/003; E21D 1/00; E21D 3/00; E21D 5/00; E21D 7/00; E21D 8/00; E21D 9/00; E21D 11/00; E21D 13/00; E21D 15/00; E21D 17/00; E21D 19/00; E21D 20/00; E21D 21/00; E21D 23/00; E21F 11/00; E21F 17/18; E21F 3/00; E21F 1/00; E21F 5/00; E21F 7/00; E21F 9/00; G06F 18/214; G06F 18/22; G06F 18/2431; G06F 18/241; G06F 18/40; G06F 30/27; G06F 1/00; G06F 3/00; G06F 5/00; G06F 7/00; G06F 8/00; G06F 9/00; G06F 11/00; G06F 12/00; G06F 15/00; G06F 13/00; G06F 16/00; G06F 17/00; G06F 18/00; G06F 21/00; G06F 30/00; G06F 40/00; G06F 2101/00; G06F 2111/00; G06F 2113/00; G06F 2115/00; G01N 2223/616; G01N 23/22; G01N 23/225; G01N 33/24; G01N 1/00; G01N 3/00; G01N 5/00; G01N 7/00; G01N 9/00; G01N 11/00; G01N 13/00; G01N 15/00; G01N 17/00; G01N 19/00; G01N 21/00

USPC ........... 340/991–994, 995.1, 995.11, 995.17, 340/426.22, 426.19, 447, 539.22, 539.13, 340/552, 680, 690

See application file for complete search history.

(56) References Cited

U.S. PATENT DOCUMENTS

| | | | | |
|---|---|---|---|---|
| 2008/0040086 | A1* | 2/2008 | Betancourt ........... | E21B 49/088<br>73/152.28 |
| 2014/0278117 | A1* | 9/2014 | Dobin .................... | G01V 1/345<br>702/16 |
| 2014/0297186 | A1 | 10/2014 | Suarez-Rivera et al. | |
| 2015/0301012 | A1 | 10/2015 | Quevedo-Cubillos et al. | |
| 2016/0195638 | A1 | 7/2016 | Ly | |
| 2018/0347354 | A1* | 12/2018 | Li .......................... | G06N 20/00 |
| 2021/0140298 | A1 | 5/2021 | Bakulin et al. | |
| 2022/0004919 | A1* | 1/2022 | Zhang ................. | G06F 18/2431 |
| 2022/0324737 | A1* | 10/2022 | Ozair ........................ | C02F 9/20 |
| 2023/0213494 | A1* | 7/2023 | Sanden .................. | G01N 33/24<br>73/865.8 |

OTHER PUBLICATIONS

John C. Davis, *Chapter 11, Electrofacies in Reservoir Characterization*, 2018, pp. 211-223.

Martin K. Dubois et al., *Comparison of Four Approaches to a Rock Facies Classification Problem*, Computers & Geosciences, vol. 33, 2007, pp. 599-617.

Touhid Mohammad Hossain et al., *Machine Learning in Electrofacies Classification and Subsurface Lithology Interpretation: A Rough Set Theory Approach*, Applied Sciences, Aug. 27, 2020, pp. 1-16.

Stefanie N. Frelinger et al., *Scanning Electron Microscopy Cathodoluminescence of Quartz: Principles, Techniques and Applications* in Ore Geology, Ore Geology Reviews, vol. 65, 2015, pp. 840-852.

Mahdi Ammar et al., *Design and Calibration of a Dual-Spectroscopy Imaging System for Rock Characterization*, Proc. of SPIE, vol. 12909, Mar. 13, 2024, pp. 1-9, XP060201216.

* cited by examiner

FIG. 5

| Lithofacies code | Lithofacies description | Lithofacies criteria (Brightness) |
|---|---|---|
| 1a | strongly confined channel axis, probably stacked | Brightness >90 |
| 1b | weakly confined channel | Brightness 80.00 – 89.99 |
| 2a | more proximal overbank, probably unconfined/levee | Brightness 68.00 – 79.99 |
| 2b | unconfined overbank/sheet sand | Brightness 61.00 – 67.99 |
| 2c | distal fan | Brightness <60.99 |
| 3 | distal (hemi)-pelagic plain, carbonate or siliciclastic dominated | Brightness <60.99 |

FIG. 6

| Lithofacies code | Lithofacies description | Lithofacies criteria (Brightness + elemental data) |
|---|---|---|
| 1a | strongly confined channel axis, probably stacked | Brightness >90 + strong oxic indicators |
| 1b | weakly confined channel | Brightness 80.00 ~ 89.99 + weak to moderate oxic indicators |
| 2a | more proximal overbank, probably unconfined/levee | Brightness 68.00 ~ 79.99 + weak anoxic indicators |
| 2b | unconfined overbank/sheet sand | Brightness 61.00 ~ 67.99 + weak anoxic indicators |
| 2c | distal fan | Brightness <60.99 + weak anoxic indicators (EFV < 0.36) |
| 3a | distal (hemi)-pelagic plain, carbonate dominated | Brightness <60.99 + strong anoxic indicators (EFV >0.36) |
| 3b | distal (hemi)-pelagic plain, siliciclastic dominated | Brightness <60.99 + strong anoxic indicators (EFV > 0.36) |

GEOLOGICAL SAMPLE INTERPRETATION THROUGH SYSTEMATIC ANALYSIS OF COLOUR, ELEMENTAL DATA AND ELECTROMAGNETIC OBSERVATION

CROSS-REFERENCE TO RELATED APPLICATIONS

This application claims priority to Italian Application No. 102022000015648, filed Jul. 26, 2022 which is incorporated herein by specific reference.

BACKGROUND OF THE INVENTION

Technical Field

Embodiments of the subject matter disclosed herein generally relate to the field of hydrocarbon prospecting and extraction. In particular, the embodiments disclosed herein relate to an apparatus, method, and system for determining the interpretation/classification of geological materials and adjusting regional maps in response to the resulting interpretation/classification.

Background of the Invention

In the field of subsurface geological characterization, identifying and interpreting different types of geological material is a key component. Traditionally the methods used for this involve the grouping of a series of geological samples into litho-types, or lithofacies. As individual rock samples, even from the same geological Formation, still show subtle differences in their composition, the ability to group geological facies into different classes of lithofacies makes it easier for scientists to interpret regional understanding of the sub-surface geology. However, in the past this method has involved both quantitative, such as elemental data capture, and qualitative, such as microscopic thin-section descriptions, input data while still requiring the need for a final qualitative interpretation by a skilled operator to distinguish the different rock categories. This workflow inherently incorporates uncertainty due to the requirement for a qualitative assessment by an operator during optical inspection of thin section slides of the geologic material. Additional uncertainty is also inherent during the classification process using the input data set, again relying on the experience and skill of the operator as well as individual interpretation of the data. In the past this has led to highly variable lithotyping schemes between operators and/or companies, asset groups and even within project group members, which can impact the efficiency and operation particularly if the skilled operator changes during the lifetime of a project.

SUMMARY OF THE INVENTION

This invention disclosed herein is designed to alleviate these issues by the replacement of the human inspection of the geological samples, with an objective image capturing and post processing system, while also removing the human element in classification with the incorporation of a machine learning process. This invention still uses quantitative data from tools providing, but not limited to, elemental, mineralogical, image, electromagnetic, and electrical behaviour data. Therefore, providing a robust and consistent process which is transferable between companies, asset managers and project members. Additionally, this invention is capable of using geological material from a whole core through to material expelled during operation to drill wells, i.e., drill-cuttings. This is an advantage over traditional thin section analysis which are usually performed on whole cores or side-wall cores, but with the economization in the energy industry, the number and availability of cores for such an analysis continues to decline.

An apparatus and method for the objective classification of geological materials based on a set of input metrics, including the training of a machine learning process to derive a consistent classification system. In certain embodiments of the apparatus, would consist of a detector surface sensitive to electromagnetic radiation and connected to an electronic system to collect and store machine readable data. In certain embodiments, the apparatus would also consist of a source of baryonic or leptonic radiation which is used to irradiate a sample surface. The baryonic or leptonic radiation would then interact with the sample surface, creating reflected or secondary electromagnetic radiation which then interacts with the surface sensitive to this radiation, and the resultant response from the detector surface is collected and recorded by the electronic processor system. In practical terms, one or more images of the sample are captured in electronic form.

In certain embodiments, the method for classification includes generation of an initial classification model, determination of various input metrics and determination of initial weighting for each input metric. In certain embodiments determination of the various input metrics could include elemental metric, mineralogical metric, while light colour metric (specifically the proportion of the colours Red, Green and Blue in the visible spectrum leading to the calculation of parameters such as hue, brightness and grey scale), ultraviolet (UV) colour metric, electromagnetic metric, electrical behaviour metric. The method may then include the use of a supervised machine learning process, wherein the determined weighted input metrics are given to the machine learning process, which is allowed to generate its initial results. The method could then include adjusting the initial weight parameters for the machine learning process to improve the difference between the prediction and the target model. In certain embodiments, the adjustment of the initial weighting could be supervised by an operator, while in certain embodiments the adjustment could be unsupervised.

The method may also include the use of the trained machine learning process on unknown samples to generate consistent rock classification of the samples.

According to a first aspect, the invention refers to a method for the classification of geological materials into similar facies.

Preferably, the method comprises determining a quantitative colour metric for each geological sample from a geographical location.

Preferably, the method comprises setting an initial classification framework based on the colour metric.

Preferably, the method comprises setting the initial classification framework based on the availability and quality of the colour metric.

Preferably, the method comprises using the initial classification framework as the target for a machine learning process, thereby obtaining a trained machine learning process.

Preferably, the method comprises applying the trained machine learning process on geological samples from another geographical location for the classification of said geological samples from another geographical location.

According to a second aspect, the invention refers to an electronic system for the classification of geological materials into similar facies.

Preferably, said electronic system is configured for determining a quantitative colour metric for each geological sample from a geographical location.

Preferably, said electronic system is configured for setting an initial classification framework based on the colour metric.

Preferably, said electronic system is configured for setting the initial classification framework based on the availability and quality of the colour metric.

Preferably, said electronic system is configured for using the initial classification framework as the target for a machine learning process, thereby obtaining a trained machine learning process.

Preferably, said electronic system is configured for receiving detection data representative of geological samples from another geographical location.

Preferably, said electronic system is configured for applying the trained machine learning process on the detection data for the classification of said geological samples from another geographical location.

In one or more of the above aspects, the invention can include one or more of the following preferred features.

Preferably, provision is made to determe one or more additional metrics.

Preferably, said additional metrics comprise one or more of: an elemental metric for each geological sample from a geographical location; a mineralogical metric for each geological sample from a geographical location; an electromagnetic metric for each geological sample from a geographical location; an electrical behaviour metric for each geological sample from a geographical location.

Preferably, said initial classification framework is set based also on the one or more additional metrics.

Preferably, the colour metric is acquired using a range of electromagnetic wavelengths.

Preferably, the colour metric is used to derive secondary metrics of brightness, grey-scale and luminosity.

Preferably, the machine learning process involves a supervised process for training the algorithm.

Preferably, the trained machine learning process is applied to unknown samples to classify into consistent rock classifications.

Preferably, in order to apply the trained machine learning process on geological samples from another geographical location, an electromagnetically sensitive surface is provided.

Preferably, the electromagnetically sensitive surface is connected to an electronic system to collect and save data.

Preferably, provision is made to expose the electromagnetically sensitive surface to the electromagnetic emissions from one or more of said geological samples from another geological location.

Preferably, provision is made to activate said electronic system to obtain a 2D or 3D output from the electromagnetically sensitive surface.

Preferably, provision is made to activate said electronic system to parse the 2D or 3D output into a red, green, and blue metric.

Preferably, provision is made to activate said electronic system to calculate the derivatives called brightness, grey scale and luminosity metrics.

Preferably, provision is made to activate said electronic system to obtain said one or more additional metrics.

Preferably, the electromagnetically sensitive surface is configured to measure a wide wavelength of electromagnetic radiation.

Preferably, provision is made to expose the sample surface to different wavelengths of electromagnetic radiation.

Preferably, provision is made to measure the emissions from the sample after being irradiated by different wavelengths and composition of baryonic and leptonic radiation.

Preferably, provision is made to determine an initial set of geological classifications based on reference data.

Preferably, provision is made to determine an initial weighting of each input metric to be used in the classification process.

Preferably, provision is made to define a final classification target for the initial geological samples data set.

Preferably, in order to use the initial classification framework as the target for the machine learning process, provision is made to train the machine learning process to achieve the final classification target using the input metrics.

Preferably, in order to determine the initial set of geological classification, provision is made to process classification from historic sources.

Preferably, in order to define the final classification target for the initial geological sample data set, provision is made to compute the initial geological classification against initial weighting of each input metric.

Preferably, in order to train the machine learning process, provision is made to input the initial geological classification, initial weighting of each metric, input metrics, initial input metric weighting into a computing device configured to process a final classification.

Preferably, provision is made to compare the results from the machine learning process to the final classification target.

Preferably, provision is made to adjust the initial weighting on the input metric to reduce the difference between the final classification target and the machine learning output.

Preferably, provision is made to repeat the training of the machine learning process until a threshold is achieved between the difference between the final classification target and the machine learning output.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 5 shows an examplary embodiment wherein classification is made based on brightness metric.

FIG. 6 shown as exemplary embodiment wherein classification is made based on brightness metric and elemental metric.

DETAILED DESCRIPTION OF PREFERRED EMBODIMENTS OF THE INVENTION

The following description of the exemplary embodiments refers to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures, or characteristics may be combined in any suitable manner in one or more embodiments.

As used herein the term "metric" refers to a measurement of a particular characteristic or attribute of an object or an index derived from multiple measurements related to a characteristic or attribute of an object. For example, multiple and repeated measurements may be obtained for geological samples and used or processed to provide one or more elemental metrics and one or more mineralogical metrics and one or more colour metrics and one or more electromagnetic metrics and one or more electrical behavior metrics for the samples.

As used herein, the term "elemental" is meant to include the total amount of chemical elements present in the geological sample, either as absolute mass percent or as a relative normalised volume percent. This would also include mass percent of a combination of indiviudal chemical elements, for example mixtures of carbon, oxygen and hydrogen normal to hydrocarbon material.

As mentioned in the background section, providing an objective and consistent rock classification model could significantly improve understanding of regional geology and improve success rate in drilling productive hydrocarbon wells. As detailed herein, one or more white light colour metric that describes the hue, brightness and grey scale of a geological sample, one or more UV light colour metric that describes the luminance of a geological sample, one or more elemental metric that describes the elemental composition of a geological sample, one or more mineralogical metric that describes the mineralogical composition of a geological sample, and one or more electromagnetic metric which describes the natural electromagnetic emission of a geological sample, and one or more electrical behavior metric which describes the response of a geological sample from the exposure to an electrical potential are used to train a machine learning process to generate a consistent rock classification model.

Figure 1:
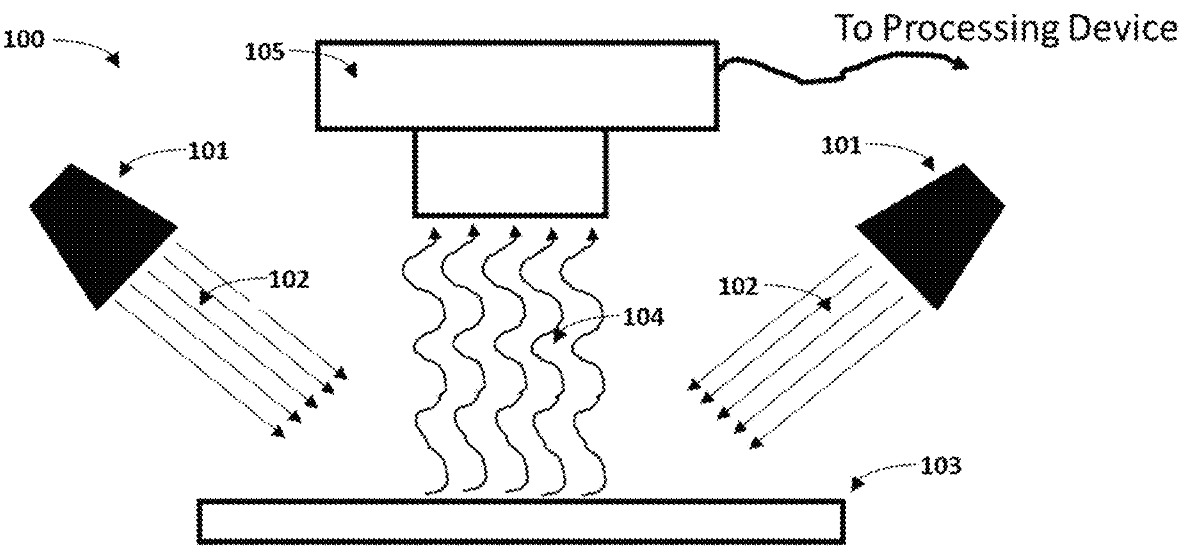
FIG. 1 is a schematic diagram depicting the irradiation and measurement of electromagnetic radiation of a geological sample to generate the colour metric.

FIG. 1 is a schematic diagram depicting one embodiment of a measurement apparatus 100 for collecting the quantitative colour metric. As depicted, the apparatus 100 includes one or more source 101 of baryonic or leptonic radiation 102, which is allowed to irradiate the surface of one or more geological samples 103, which causes the geological sample 103 to either reflect or generate secondary electromagnetic radiation 104. The secondary electromagnetic radiation 104 then reacts with a surface sensitive to a wide range of electromagnetic radiation 105, and the electromagnetic sensitive surface 105 is connected to a processing device 200 which records, stores and processes the output from the secondary electromagnetic radiation 104 into a quantitative colour metric.

One of skill in the art will appreciate that the functionality provided by the modules of the apparatus 100 may be achieved with a variety of implementations. The functionality may be partitioned in a variety of ways resulting in a variety of modules that collectively provide the described functionality. The images generated therewith may be used to determine of variety of colour metrics and other results for the corresponding geological samples.

Figure 2:
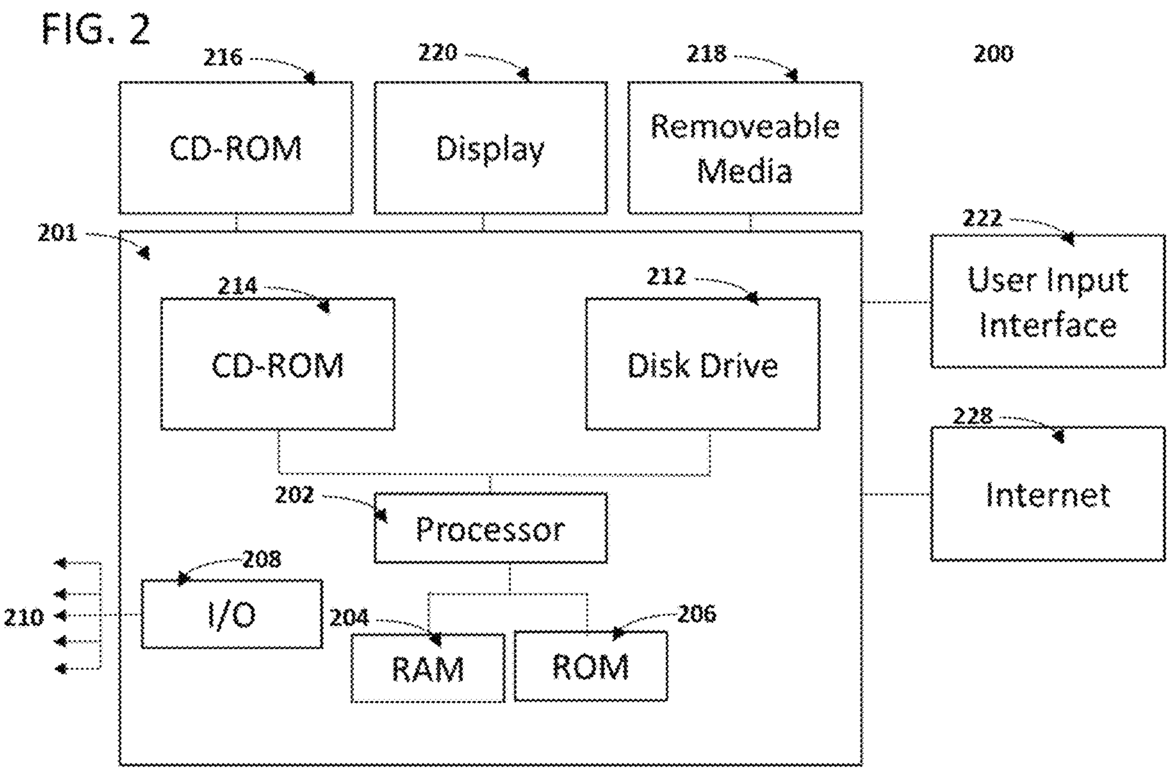
FIG. 2 is a block diagram of a computing device for processing classification metric for geological samples.

FIG. 2 is a block diagram of an electronic system (or processing device) 200 for performing the activities herein disclosed and claimed.

The processing device 200 may include a server 201. Such a server 201 may include a central processor (CPU) 202 coupled to a random-access memory (RAM) 204 and to a read-only memory (ROM) 206. The ROM 206 may also be other types of storage media to store programs, such as programmable ROM (PROM), erasable PROM (EPROM), etc. The processor 202 may communicate with other internal and external components through input/output (I/O) circuitry 208 and bussing 210, to provide control signals and the like. The processor 202 carries out a variety of functions as are known in the art, as dictated by software and/or firmware instructions.

The server 201 may also include one or more data storage devices, including hard drives 212, CDDROM drives 214, and other hardware capable of reading and/or storing information such as DVD, etc. In one embodiment, software for carrying out the above-discussed steps may be stored and distributed on a CDDROM or DVD 216, a USB storage device 218 or other form of media capable of portably storing information. These storage media may be inserted into, and read by, devices such as the CDDROM drive 214, the disk drive 212, etc. The server 201 may be coupled to a display 220, which may be any type of known display or presentation screen, such as LCD displays, plasma display, cathode ray tubes (CRT), etc. A user input interface 222 is provided, including one or more user interface mechanisms such as a mouse, keyboard, microphone, touchpad, touch screen, voice-recognition system, etc.

The server 201 may be coupled to other devices, such as sources, detectors, etc. The server 201 may be part of a larger network configuration as in a global area network (GAN) such as the Internet 228, which allows ultimate connection to the various landline and/or mobile computing devices.

Figure 3:
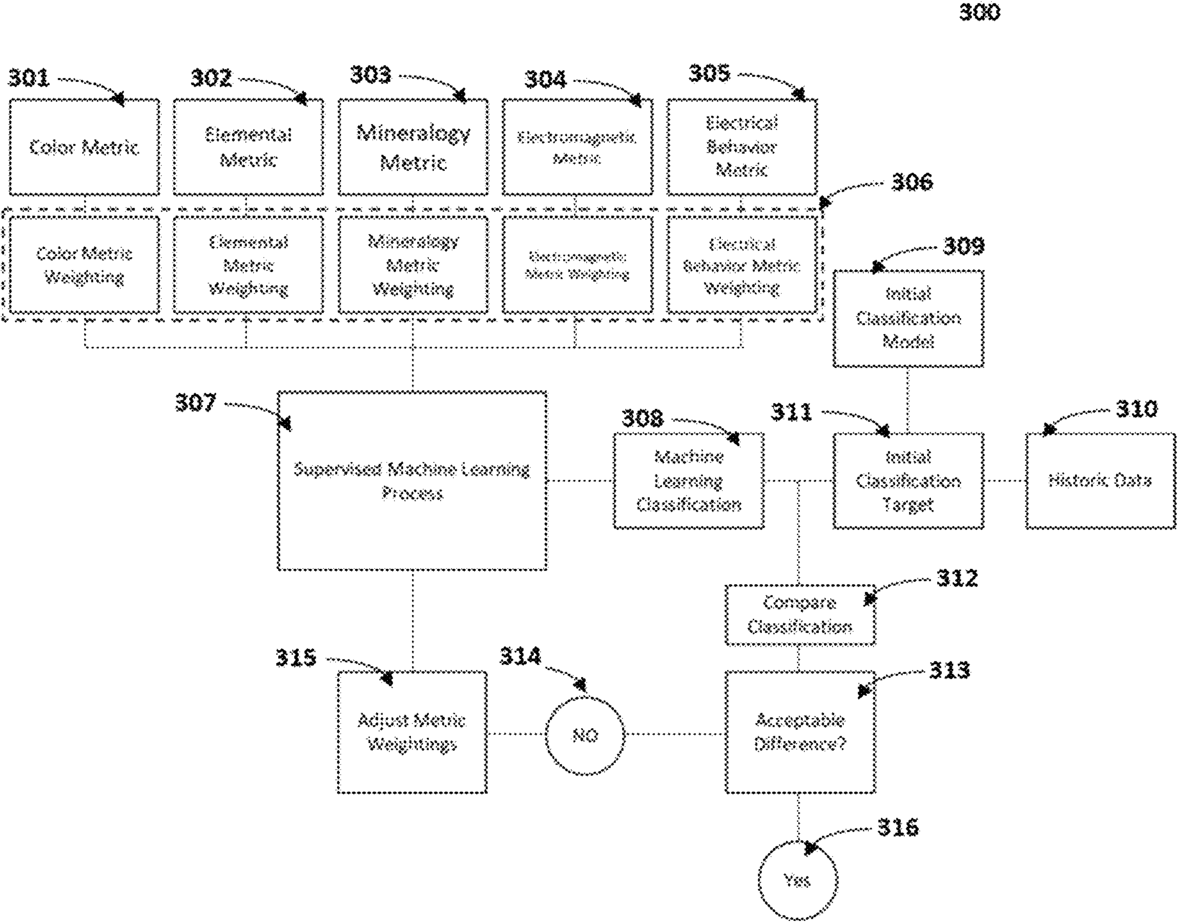
FIG. 3 is a flowchart diagram depicting one embodiment of the training of a supervised machine learning process.

FIG. 3 is a flowchart depicting one embodiment for the training of the machine learning process 300. In certain embodiments this could include the determination of a white light or UV light colour metric 301, elemental metric 302, mineralogy metric 303, electromagnetic metric 304, electrical behavior metric 305. Each of these metrics can be given an initial weighting 306, which is then used as the initial inputs into an unsupervised machine learning processor 307. The machine learning processor 307 is thus enabled to generate an initial geological material classification model 308 based on the initial weighting 306. Additionally, in certain embodiments, an initial classification target 311 is determined using an initial classification model 309 and reference data and interpretation 310. The reference data can be historical data, i.e., previously collected data (data collected in the past) and used to build a model. The initial classification target 311 is then compared 312 to the initial machine learning classification 308, and the difference between these two classifications 313 is then assessed if it is within a define threshold. In the case the difference between these two classifications 313 is greater than the defined threshold 314, the initial metric weightings are adjusted 315 with the aim of reducing the difference. The adjusted weighting 315 are then applied to the input metrics (301, 302, 303, 304, 305), and reinputted into the machine learning process 307, which then generates an updated geological classification 311. This process of comparing 312 the machine learning classification 308 to the initial classification target 311 and adjustment of the metric weights 315 is then repeated until the difference between the two classifications 313 is within the acceptable threshold 316.

Following the training of the machine learning process, unknown samples from different wells from different geographic locations can then be processed to generate a robust and consistent rock classification.

Figure 4:
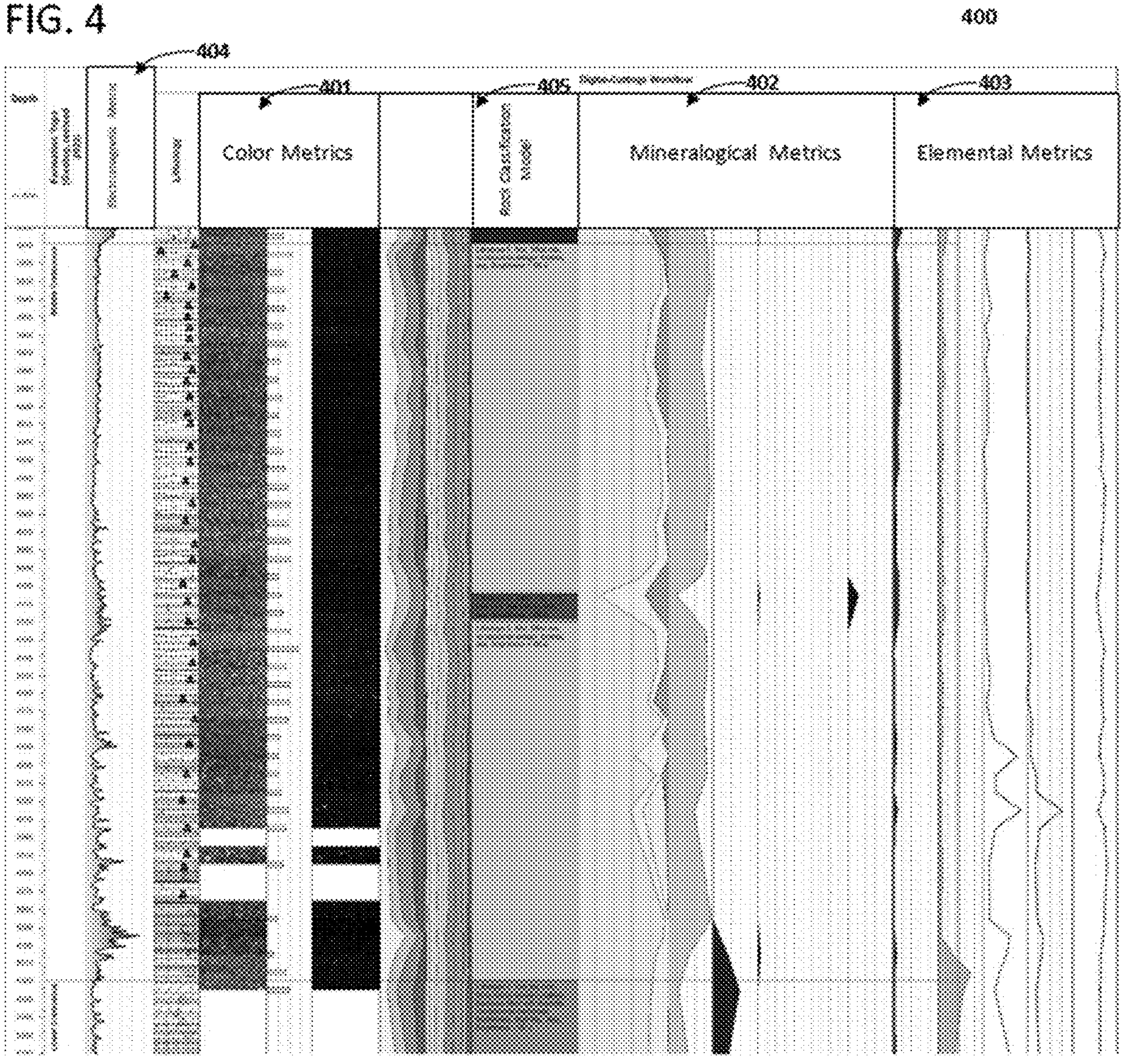
FIG. 4 is a diagram showing the results from the processing of an unknown well with a trained machine learning processor leveraging the present invention.

FIG. 4 exemplifies the results from the processing of an unknown well with a trained machine learning processor 400. In certain embodiments, the output could include the input white light and/or UV light colour metric 401, mineralogical metric 402, elemental metric 403, electromagnetic metric 404. The resultant rock classification model 405 could then be displayed as different colours or patterns for a group of geological material with similar metric parameters. The advantage of the results from this invention is exemplified in output 405, wherein the resultant classification uses a brightness metric, derived from the colour metric, which is not possible with the current state of art. In other embodiments, the output rock classification model could include other metric derived from the colour metric, including but not limited to, a red metric and or a green metric and or a blue metric and or a luminosity metric.

From a general perspective, the Applicant observes that the invention can be implemented based on the colour metric (e.g., brightness or grey-scale. Such metric is used to generate an initial lithofacies or lithotype classification of the geological samples in a particular bore-hole from a particular field, basin or geological region. The model can be further refined with further acquired data (e.g., data from a new drilled well), which are incorporated into the scheme to further train the model and improve knowledge and accuracy of the same.

FIG. 5 shown an exemplary embodiment, wherein classification has been build based on the brightness metric only.

As said above, in preferred embodiments, one or more additional metrics are combined with the colour metric for enhancing the system performance. In this respect, FIG. 6 shows an exemplary embodiment, which stems from the example of FIG. 5, wherein also an elemental metric has been used. The Applicant observes that, in addition to enhancing the reliability of the classification, the use of the elemental metric in addition to the colour (brightness) metric allows defining a further level of classification: whereas in FIG. 5 the range defined by Brightness <60.99 corresponds to a single level (code "3"), which includes distal (hemi)-pelagic plain, carbonate or siliciclastic dominated, in FIG. 6 two distinct levels are defined, namely "3a" and "3b", corresponding to distal (hemi)-pelagic plain, carbonate dominated and distal (hemi)-pelagic plain, siliciclastic dominated, respectively.

More generally, other acquired datasets (elemental, mineralogical, electromagnetic etc.) can be used to further refine the initial classification to generate a final lithofacies/lithotype classification which is then applied to the entire dataset for that particular field, basin or geological region. With more acquired data (e.g., data from a new drilled well) additional training can be performed.

In summary, the methods, apparatuses, and processes presented herein provide a number of distinct advantages over prior art method, apparatus and process. It should be noted that many of the functional units described herein such as those related to machine learning training are identified as modules. Others are assumed to be modules. One of skill in the art will appreciate that the various modules described herein may include a variety of hardware components that provide the described functionality including one or more processors such as CPUs or microcontrollers that are configured by one or more software components. The software components may include executable instructions or codes and corresponding data that are stored in a computer-readable storage medium such as a non-volatile memory, or the like. The instructions or codes may include machine codes that are configured to be executed directly by the processor. Alternatively, the instructions or codes may be configured to be executed by an interpreter, or the like, that translates the instructions or codes to machine codes that are executed by the processor.

It should also be understood that this description is not intended to limit the invention. On the contrary, the exemplary embodiments are intended to cover alternatives, modifications, and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

The invention claimed is:

1. A method for the classification of geological materials into similar facies, the method comprising:

- determining a quantitative colour metric for each geological sample from a geographical location;
- setting an initial classification framework based on the availability and quality of the colour metric;
- using the initial classification framework as the target for a machine learning process, thereby obtaining a trained machine learning process; and
- applying the trained machine learning process on geological samples from another geographical location for the classification of said geological samples from another geographical location;
- wherein applying the trained machine learning process on geological samples from another geographical location further comprises:
  - providing an electromagnetically sensitive surface, connected to an electronic system to collect and save data;
  - exposing the electromagnetically sensitive surface to the electromagnetic emissions from one or more of said geological samples from another geological location; and
  - activating said electronic system to obtain a 2D or 3D output from the electromagnetically sensitive surface, and parse this data into a red, green, and blue metric, and then calculate the derivatives called brightness, grey scale and luminosity metrics.

2. The method of claim 1, further comprising:
determining one or more additional metrics, said additional metrics comprising one or more of: an elemental metric for each geological sample from a geographical location; a mineralogical metric for each geological sample from a geographical location; an electromagnetic metric for each geological sample from a geographical location; an electrical behaviour metric for each geological sample from a geographical location;
wherein said initial classification framework is set based also on the one or more additional metrics.

3. The method of claim 1, wherein the colour metric is acquired using a range of electromagnetic wavelengths.

4. The method of claim 1, wherein colour metric is used to derive secondary metrics of brightness, grey-scale and luminosity.

5. The method of claim 1, wherein the trained machine learning process is applied to unknown samples to classify into consistent rock classifications.

6. The method according to claim 5, further comprising activating said electronic system to obtain said one or more additional metrics.

7. The method of claim 5, wherein the electromagnetically sensitive surface is configured to measure a wide wavelength of electromagnetic radiation.

8. The method of claim 1, further comprising:
exposing the sample surface to different wavelengths of electromagnetic radiation;
measuring the emissions from the sample after being irradiated by different wavelengths and composition of baryonic and leptonic radiation.

9. A method for the classification of geological materials into similar facies, the method comprising:
determining a quantitative colour metric for each geological sample from a geographical location;
setting an initial classification framework based on the availability and quality of the colour metric;
using the initial classification framework as the target for a machine learning process, thereby obtaining a trained machine learning process;
applying the trained machine learning process on geological samples from another geographical location for the classification of said geological samples from another geographical location;
wherein the machine learning process involves a supervised process for training the algorithm, further comprising:
determining an initial set of geological classifications based on reference data;
determining an initial weighting of each input metric to be used in the classification process;
defining a final classification target for the initial geological samples data set;
wherein using the initial classification framework as the target for the machine learning process comprises training the machine learning process to achieve the final classification target using the input metrics.

10. The method of claim 9, wherein determining the initial set of geological classification comprises processing classification from historic sources.

11. The method of claim 9, wherein defining the final classification target for the initial geological sample data set comprises the computation of the initial geological classification against initial weighting of each input metric.

12. The method of claim 9, wherein training the machine learning process comprises inputting the initial geological classification, initial weighting of each metric, input metrics, initial input metric weighting into a computing device configured to process a final classification.

13. The method of claim 12, wherein the results from the machine learning process is compared to the final classification target, and the initial weighting on the input metric are adjusted to reduce the difference between the final classification target and the machine learning output.

14. The method of claim 13, wherein the training of the machine learning process is repeated until a threshold is achieved between the difference between the final classification target and the machine learning output.

15. An electronic system for the classification of geological materials into similar facies, said electronic system being configured for:
determining a quantitative colour metric for each geological sample from a geographical location;
setting an initial classification framework based on the availability and quality of the colour metric;
using the initial classification framework as the target for a machine learning process, thereby obtaining a trained machine learning process;
receiving detection data representative of geological samples from another geographical location;
applying the trained machine learning process on the detection data for the classification of said geological samples from another geographical location; and
wherein applying the trained machine learning process on geological samples from another geographical location further comprises:
providing an electromagnetically sensitive surface, connected to an electronic system to collect and save data;
exposing the electromagnetically sensitive surface to the electromagnetic emissions from one or more of said geological samples from another geological location; and
activating said electronic system to obtain a 2D or 3D output from the electromagnetically sensitive surface, and parse this data into a red, green, and blue metric, and then calculate the derivatives called brightness, grey scale and luminosity metrics.

* * * * *